US011140918B2

(12) United States Patent
Vora et al.

(10) Patent No.: US 11,140,918 B2
(45) Date of Patent: Oct. 12, 2021

(54) PERSONAL VAPORIZER

(71) Applicant: Flair Vapor, LLC, South Plaintfield, NJ (US)

(72) Inventors: Niravkumar Vora, Edison, NJ (US); Mitul Patel, Edison, NJ (US)

(73) Assignee: Flair Products LLC, South Plainfield, NJ (US)

( * ) Notice: Subject to any disclaimer, the term of this patent is extended or adjusted under 35 U.S.C. 154(b) by 326 days.

(21) Appl. No.: 16/354,855

(22) Filed: Mar. 15, 2019

(65) Prior Publication Data

US 2020/0288788 A1  Sep. 17, 2020

(51) Int. Cl.
*A24F 40/40* (2020.01)
*A61M 15/06* (2006.01)

(52) U.S. Cl.
CPC ............. *A24F 40/40* (2020.01); *A61M 15/06* (2013.01)

(58) Field of Classification Search
CPC .................................................. A24F 47/008
USPC ......................................................... 131/329
See application file for complete search history.

(56) References Cited

U.S. PATENT DOCUMENTS

| | | |
|---|---|---|
| D537,609 S | 3/2007 | Horowitz |
| D692,615 S | 10/2013 | Verleur et al. |
| D693,054 S | 11/2013 | Verleur et al. |
| 8,991,402 B2 | 3/2015 | Bowen et al. |
| D736,995 S | 8/2015 | Recio |
| D742,063 S | 10/2015 | Recio |
| D744,419 S | 12/2015 | Bowen et al. |
| 9,215,895 B2 | 12/2015 | Bowen et al. |
| D749,505 S | 2/2016 | Verleur et al. |
| D750,320 S | 2/2016 | Verleur et al. |
| D752,278 S | 3/2016 | Verleur et al. |
| D752,280 S | 3/2016 | Verleur et al. |
| D762,003 S | 7/2016 | Lomeli |
| D763,502 S | 8/2016 | Verleur et al. |
| 9,408,416 B2 | 8/2016 | Monsees et al. |
| D776,338 S | 1/2017 | Lomeli |
| 9,549,573 B2 | 1/2017 | Monsees et al. |
| D788,697 S | 6/2017 | Verleur et al. |
| D790,127 S | 6/2017 | Verleur |
| D800,383 S | 10/2017 | Verleur et al. |

(Continued)

FOREIGN PATENT DOCUMENTS

| | | |
|---|---|---|
| AU | 20129201728 A1 | 4/2019 |
| CA | 162263 S | 4/2016 |

(Continued)

OTHER PUBLICATIONS

EPO Intl. Search Report for European Patent App. No. 19190385.5 dated Feb. 13, 2020.

*Primary Examiner* — Harshad C Patel
(74) *Attorney, Agent, or Firm* — BakerHostetler

(57) ABSTRACT

Systems and methods utilizing a first housing magnet of a vaporizing device cartridge port substantially oriented in a first polar configuration and a second housing magnet of the cartridge port substantially oriented in a second polar configuration, wherein the second polar configuration is substantially opposite the first polar configuration, to properly orient and seat a cartridge in a vaporizing device. Systems and methods can further include alternative or complementary aspects for imposing cartridge orientation and fit, such as mechanical interference aspects.

18 Claims, 12 Drawing Sheets

(56) References Cited

U.S. PATENT DOCUMENTS

| | | |
|---|---|---|
| 9,781,953 B2 | 10/2017 | Verleur et al. |
| D825,102 S | 8/2018 | Bowen et al. |
| D825,835 S | 8/2018 | Verleur et al. |
| D825,844 S | 8/2018 | Verleur et al. |
| 10,030,321 B1 | 8/2018 | Verleur et al. |
| 10,045,567 B2 | 8/2018 | Monsees et al. |
| 10,045,568 B2 * | 8/2018 | Monsees ................ H05B 3/44 |
| 10,058,124 B2 | 8/2018 | Monsees et al. |
| 10,058,129 B2 * | 8/2018 | Monsees ................ H05B 3/44 |
| 10,058,130 B2 * | 8/2018 | Monsees ................ A24F 7/00 |
| 10,070,669 B2 * | 9/2018 | Monsees ................ A24F 40/46 |
| 10,075,139 B2 * | 9/2018 | Nallamothu ........... H03G 3/001 |
| 10,076,139 B2 | 9/2018 | Monsees et al. |
| 10,085,481 B2 | 10/2018 | Verleur et al. |
| 10,104,915 B2 * | 10/2018 | Bowen ................ A24B 15/167 |
| 10,111,470 B2 * | 10/2018 | Monsees ................ H05B 3/44 |
| D833,064 S | 11/2018 | Verleur et al. |
| 10,117,465 B2 | 11/2018 | Monsees et al. |
| 10,117,466 B2 | 11/2018 | Monsees et al. |
| 10,130,123 B2 * | 11/2018 | Hatton .................... A24F 40/50 |
| 10,201,190 B2 | 2/2019 | Monsees et al. |
| 2011/0168194 A1 * | 7/2011 | Hon ........................ F24H 3/002 |
| | | 131/273 |
| 2015/0157056 A1 | 6/2015 | Bowen et al. |
| 2017/0020193 A1 * | 1/2017 | Davis ................... A61M 11/041 |
| 2017/0215478 A1 * | 8/2017 | Harrison ................ A24F 40/40 |
| 2018/0077967 A1 | 3/2018 | Hatton |
| 2018/0317557 A1 | 11/2018 | Monsees |

FOREIGN PATENT DOCUMENTS

| | | |
|---|---|---|
| CN | 208300942 U | 1/2019 |
| EP | 2875741 A2 | 3/2014 |
| EP | 2875740 B1 | 10/2018 |
| HK | 1210382 A1 | 4/2016 |
| WO | WO2014/182736 A1 | 11/2014 |
| WO | WO2015/073564 A1 | 5/2015 |

\* cited by examiner

PERSONAL VAPORIZER

TECHNICAL FIELD

The disclosure generally relates to vaporizing devices, and more particularly to vaporizing devices using detachable cartridges which can mount to the vaporizing devices according to a particular orientation.

BACKGROUND

Personal vaporizers, which are often referred to as "vaping" devices emerged as an alternative to traditional tobacco smoking in recent years and have exploded in popularity. Personal vaporizers may deliver an amount of nicotine contained within a liquid by heating the liquid to the point that it becomes an aerosol. This aerosol is inhaled much like smoke from a traditional cigarette. While the delivery of nicotine is one possible use for such devices, this use is not limiting.

Personal vaporizers now span a wide spectrum of features and price points. One thing vaporizers have in common for use is the need to aerosolize fluid. Fluid is typically provided in a chamber or cartridge, which also often includes a heating element to vaporize the fluid in said chamber. Certain vaporizers require users to refill a permanent or reusable chamber manually. This can be messy and creates further complexities as the heating element degrades or changes based on use and fluid residue buildup.

A variety of vaporizers therefore use removable, disposable cartridges containing fluid for vaporization and a heating element. To utilize these cartridges, they must be placed in electrical communication with the vaporizing device to power and control the heating element. Attachment of these cartridges if frequently achieved by a friction fit, snaps, or detents. To keep manufacturing costs low, personal vaporizer housings are often constructed as an extruded form that is cut to a length to accommodate the internal components of the vaporizer and provide a recess or other housing for a removable cartridge. These extruded forms are typically symmetrical in shape to avoid uneven stresses within the extrusion die and otherwise facilitate their manufacture. While this goal of reducing costs and facilitating manufacture of these devices is laudable, there are competing goals of ensuring that the cartridge is properly oriented within the device for use. Therefore, there is a need for a design that provides a unique cartridge orientation for use within the personal vaporizer as discussed in more detail below.

SUMMARY

In an example, an personal vaporizer includes a housing defined by a height extending along a first axis, a width extending along a second axis, and a depth extending along a third axis. The personal vaporizer also includes a battery, a charging assembly configured to charge the battery, and cartridge port 109 configured to accept a cartridge. The personal vaporizer further includes a first housing magnet of cartridge port 109 substantially oriented in a first polar configuration, and a second housing magnet of cartridge port 109 substantially oriented in a second polar configuration, wherein the second polar configuration is substantially opposite the first polar configuration. The personal vaporizer also includes an electrical contact of cartridge port 109.

In an example, an example method can include providing a housing for a vaporizing device having a first housing magnet and a second housing magnet. The first housing magnet is substantially oriented in a first polar configuration, and the second housing magnet is substantially oriented in a second polar configuration. The second polar configuration is substantially opposite the first polar configuration. The method can also include providing a cartridge configured to contain fluid for vaporization. The cartridge is configured to mate with the housing, and has a first cartridge magnet and a second cartridge magnet. The first cartridge magnet is configured to attract the first housing magnet and repel the second housing magnet when coupling the cartridge with the housing, and the second cartridge magnet is configured to attract the second housing magnet and repel the first housing magnet when coupling the cartridge with the housing. The method also includes coupling the cartridge with the housing according to polarities of the magnets.

Additional and alternative aspects will be apparent on review of other portions of this disclosure.

BRIEF DESCRIPTION OF DRAWINGS

So that those having ordinary skill in the art, to which the present disclosure pertains, will more readily understand how to employ the novel system and methods of the present disclosure, certain illustrated examples thereof will be described in detail herein-below with reference to the drawings, wherein.

DETAILED DESCRIPTION

Figure 1:
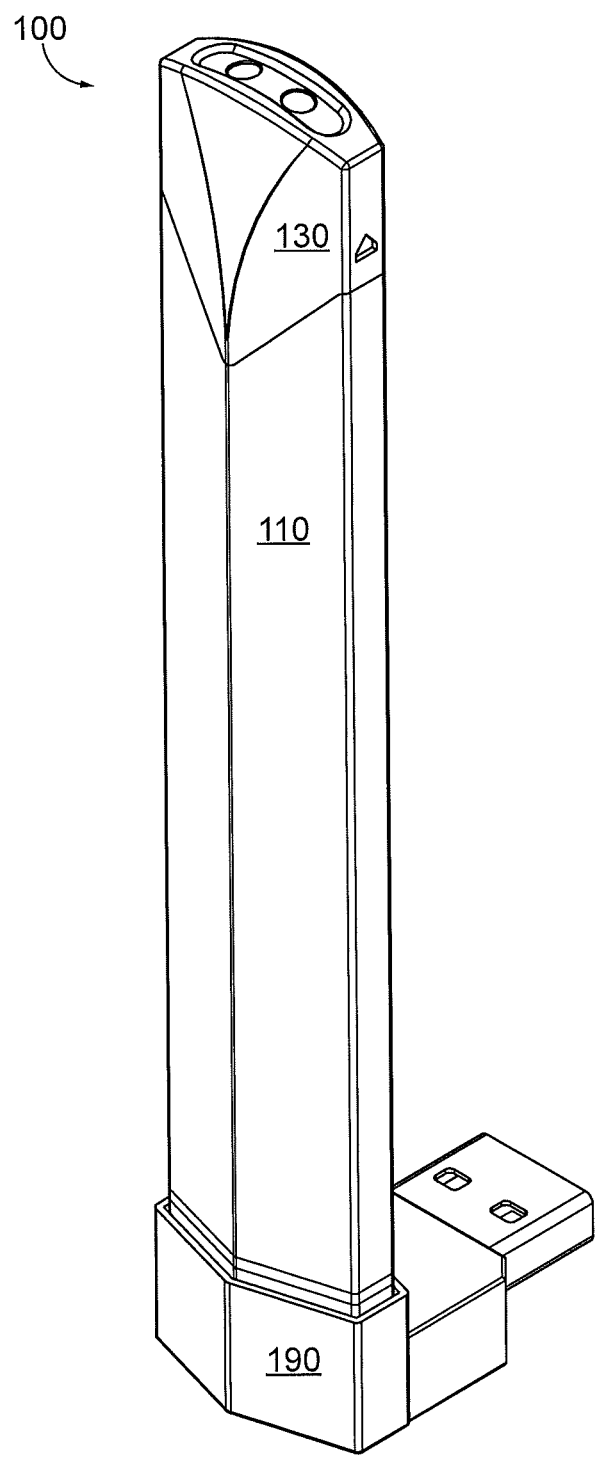
FIG. 1 illustrates a view of an example of a vaporizing device, cartridge, and charger.
Figure 2:
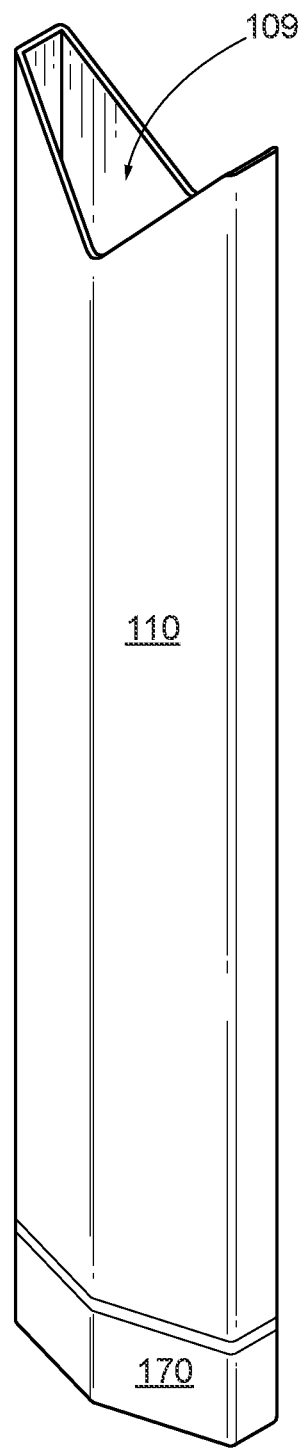
FIG. 2 illustrates a view of an example vaporizing device.
Figure 3:
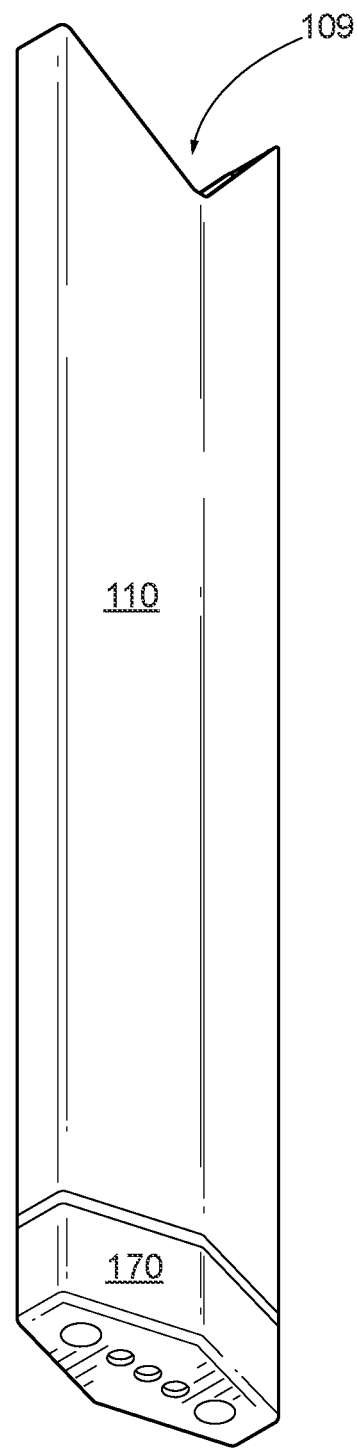
FIG. 3 illustrates another view of an example vaporizing device.
Figure 4:
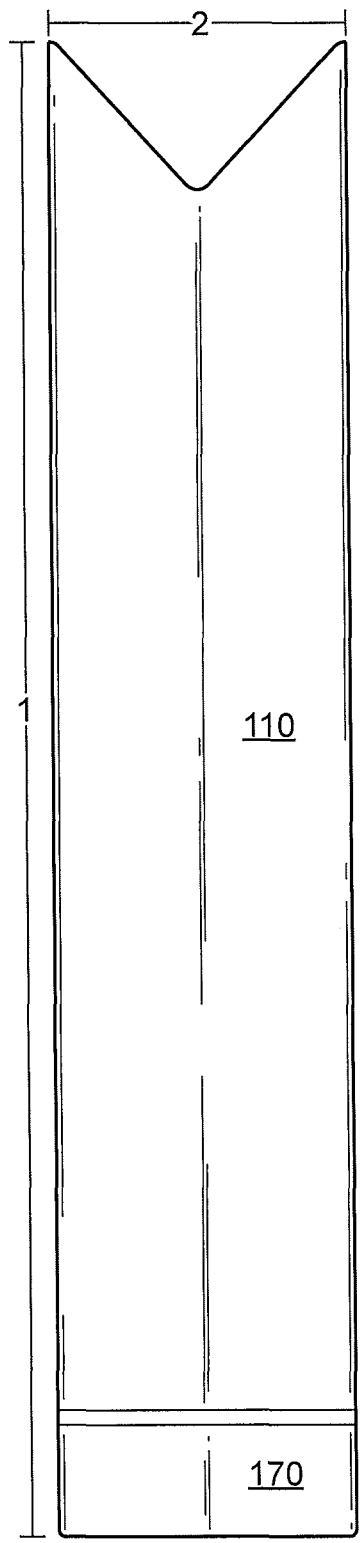
FIG. 4 illustrates another view of an example vaporizing device.
Figure 5:
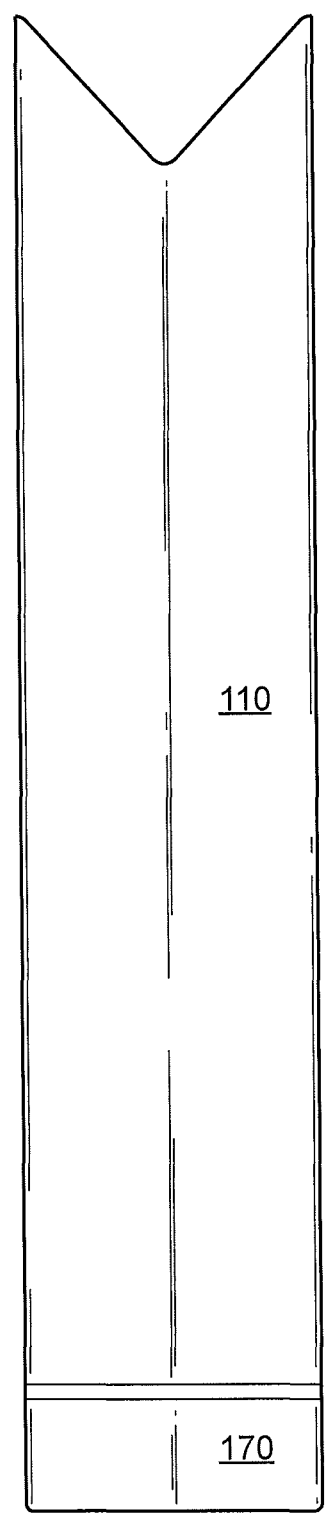
FIG. 5 illustrates another view of an example vaporizing device.
Figure 6:
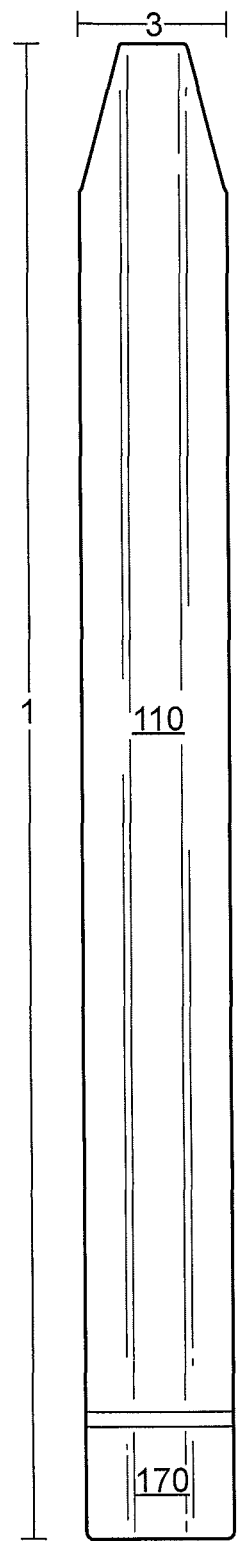
FIG. 6 illustrates another view of an example vaporizing device.
Figure 7:
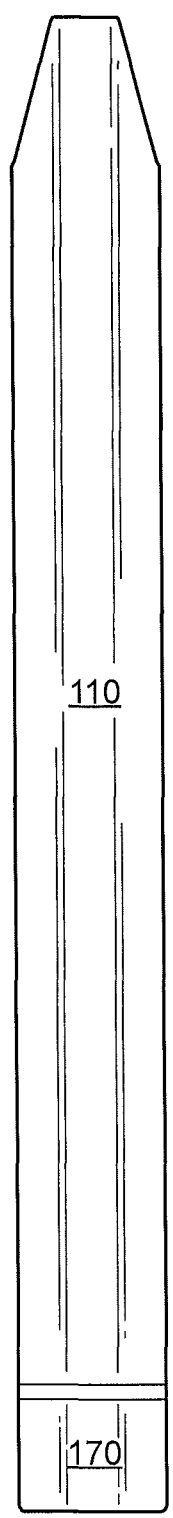
FIG. 7 illustrates another view of an example vaporizing device.
Figure 8:
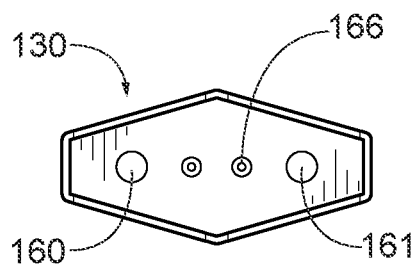
FIG. 8 illustrates another view of an example vaporizing device.
Figure 9:
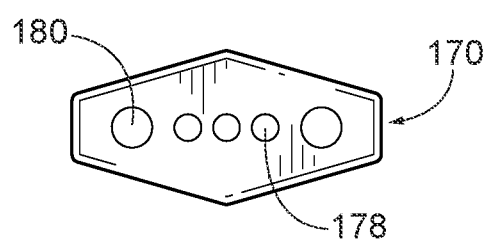
FIG. 9 illustrates another view of an example vaporizing device.
Figure 10:
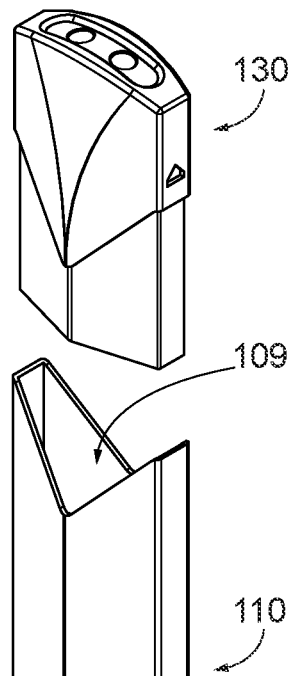
FIG. 10 illustrates a view of an example of a vaporizing device, cartridge, and charger.
Figure 10:
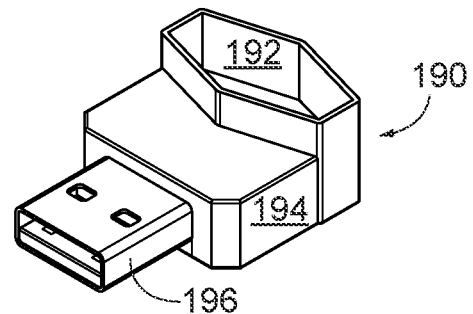

Systems and methods herein disclose vaporizing devices, uses thereof, and techniques for positively seating a disposable or reusable vaporizer cartridge in vaporizer devices according to a required or preferred orientation.

As used herein, directions or ends described as "top," "above," "over," et cetera refer to the end of housing 110 accepting cartridge 130 along first axis 1, and directions or ends described as "bottom," "below," "underneath," et cetera refer to the end of housing 110 on which charging cap 170 is arranged. A "front" side can refer to the side from which power source 196 protrudes when charging cap 170 is arranged in charger 190, which is opposite a "back" side along the third axis. Side elements can be those connecting or between the front and back sides. As can be appreciated, in alternative geometries (e.g., symmetrical cross-sections such as a square) some such distinctions are obviated, although some (e.g., top and bottom) may not be.

FIGS. 1-19 illustrate various examples of vaporizing system 100. System 100 generally includes the device, which may house the electronics that control the vaporizing process. These electronics may include a power supply and a controller. The device may include a recess, bracket or other housing for receipt of a removable cartridge described more completely below.

Vaporizing system 100 can be defined in three dimensions according to three axes, axis 1, axis 2, and axis 3, as depicted explicitly in, e.g., FIGS. 4, 6, 14, and 16. Particularly, FIGS. 1-10 show various views of a vaporizing device defined in part by housing 110 (including cutout portion 111) and charging cap 170, alone and/or in conjunction with cartridge 130 and charger 190. Details of the components illustrated are provided hereafter.

Vaporizing system 100 can be made of various materials. In embodiments, one or more of housing 110, charging cap 170, charger 190, and/or cartridge 130 can be constructed of plastics, metals, carbon fiber, or other materials, and combinations thereof. In embodiments, sub-assemblies can be formed of different materials (e.g., aluminum housing 110, polymer charging cap 170).

Figure 11:
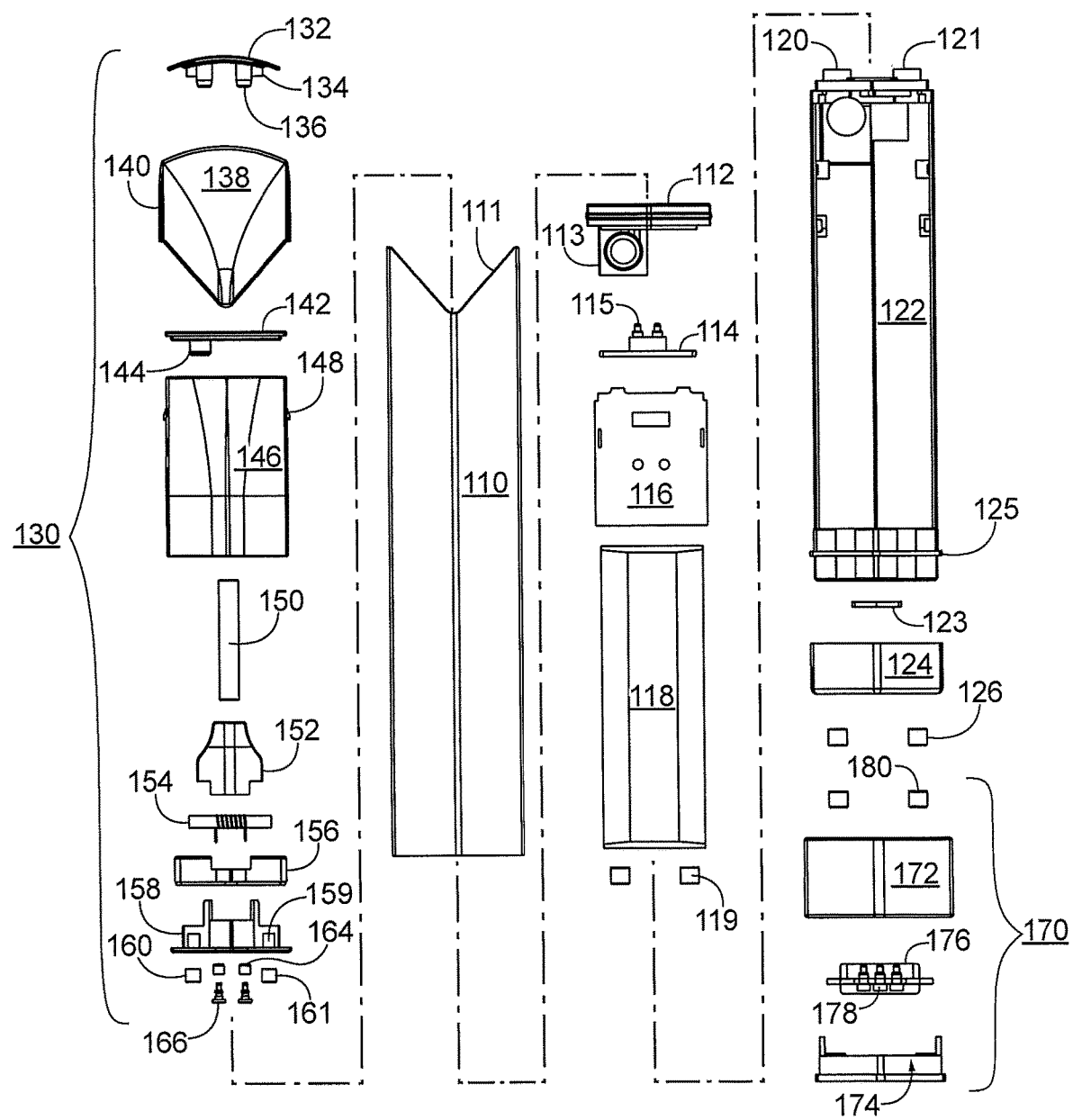
FIG. 11 illustrates an exploded view of an example vaporizing device and cartridge.
Figure 12:
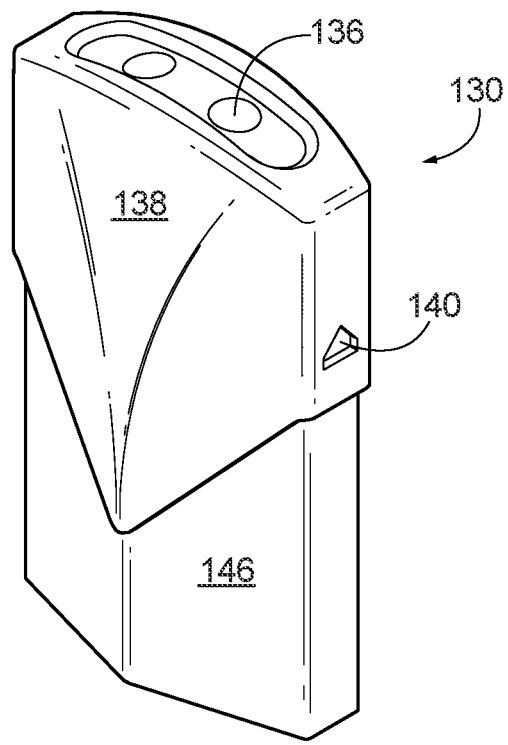
FIG. 12 illustrates a view of an example cartridge.
Figure 13:
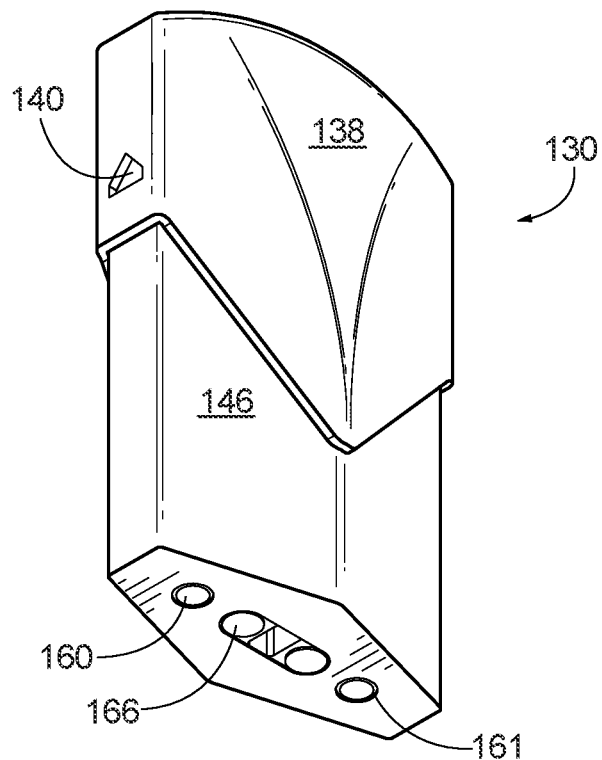
FIG. 13 illustrates another view of an example cartridge.
Figure 14:
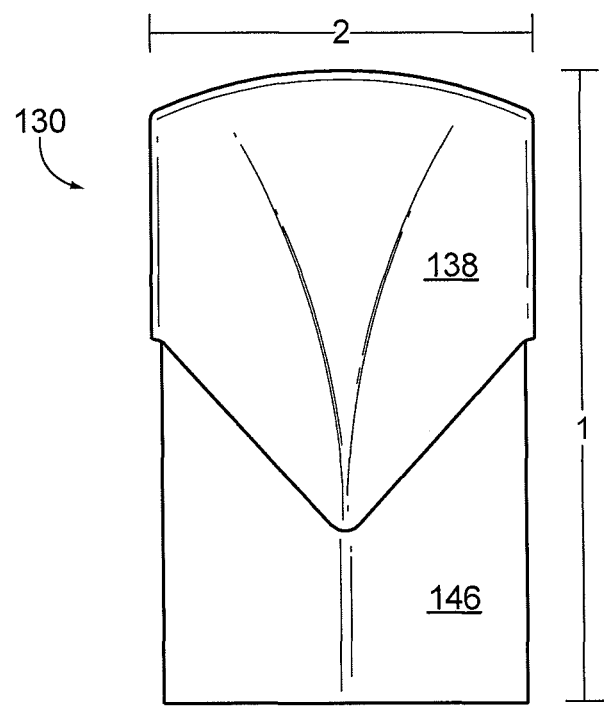
FIG. 14 illustrates another view of an example cartridge.
Figure 15:
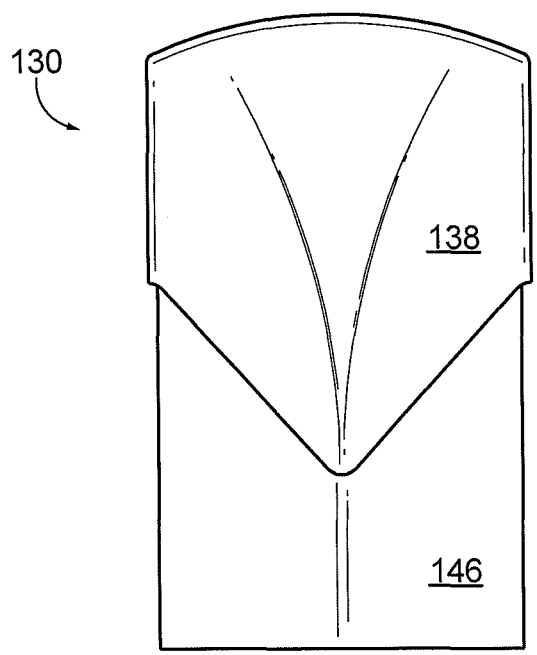
FIG. 15 illustrates another view of an example cartridge.
Figure 16:
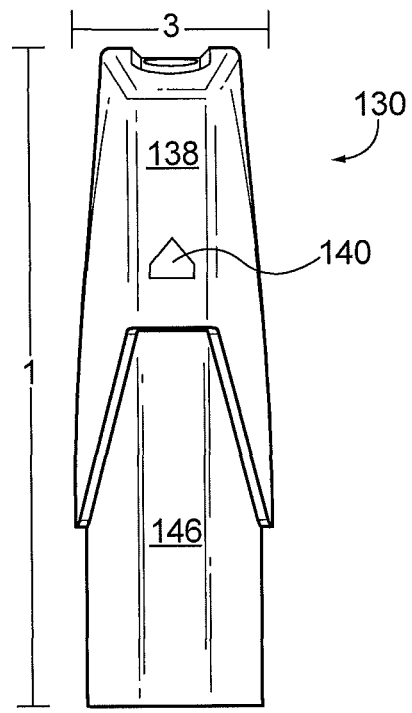
FIG. 16 illustrates another view of an example cartridge.
Figure 17:
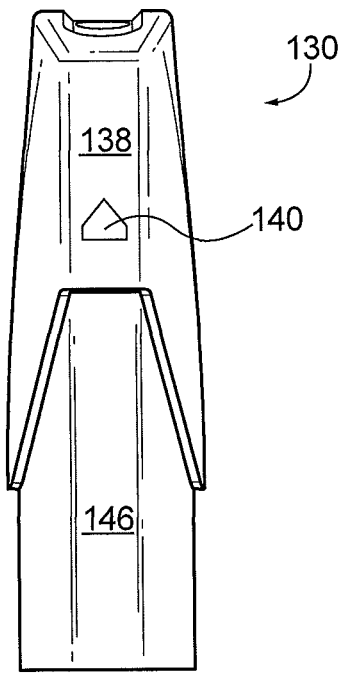
FIG. 17 illustrates another view of an example cartridge.
Figure 18A:
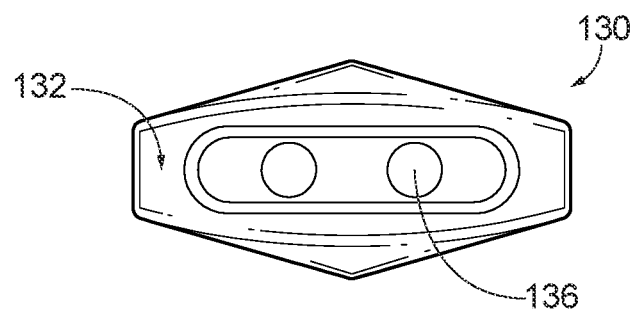
FIG. 18A illustrates another view of an example cartridge.
Figure 18B:
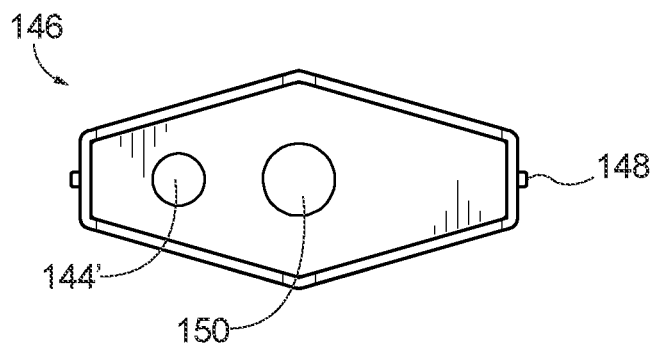
FIG. 18B illustrates another view of an example cartridge.
Figure 19:
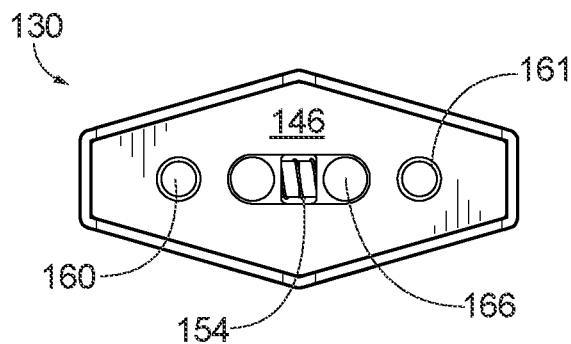
FIG. 19 illustrates another view of an example cartridge.

FIG. 11 provides an exploded view of the vaporizing device and cartridge 130. Many components of the vaporizing device are contained within housing 110, which is defined by a height extending along a first axis 1, a width extending along a second axis 2, and a depth extending along a third axis 3. Housing 110 can have a substantially and irregularly hexagonal cross-section (i.e., on a plane defined by the second axis 2 and third axis 3). Alternative embodiments can utilize any shape within the imagination of the designer, including squares, rectangles, and other regular or irregular polygons, curved or partially-curved contours, triangular arrangements, et cetera. The vaporizing device is elongate along first axis 1, with its length defined in part by charging cap 170. Housing 110 includes a solid portion and cutout portion 111, with cutout portion 111 and, in embodiments, a portion of space there below comprising a hollow portion of housing 110 defining cartridge port 109 in which cartridge 130 nests or mounts for use with the vaporizing device. In embodiments, housing 110 need not be elongate, but may have other form factors (e.g., cube, spherical, et cetera) as can be imagined by the designer. Housing 110 (or other elements herein) can be formed of insulating materials to prevent the external surfaces of the vaporizing device from becoming hot. As illustrated, housing 110 can be defined by a plurality of walls extending along or past one or both of solid (e.g., containing electrical and other components of the vaporizer device) and hollow (e.g., port for accepting cartridge 130 or other empty space) portions. As illustrated, there can be larger front and rear walls comprising bends (e.g., first and second walls front walls extending primarily in along second axis 2) and smaller side walls connecting the larger walls (e.g., third and fourth side walls extending primarily along third axis 3 and first axis 1). Alternatively, each planar surface can define a wall (e.g., first, second, third, and fourth walls extending primarily along second axis 2 and first axis 1, and fifth and sixth walls extending primarily along the third axis 3 and first axis 1). In alternative embodiments, the ratios of wall dimensions can vary to support other shapes described herein.

As described above, housing 110 and/or cartridge 130 may incorporate a lack of symmetry to ensure proper orientation of cartridge 130 relative to housing. Asymmetry may be achieved in a variety of manners. For example, housing 110 can be flared, tapered, stepped, or having different contours or shapes when comparing a first side to its opposite side (in one or more of height, width, and depth). Cartridge 130, or portions thereof, can be shaped to join with the asymmetrical housing 110. Further, cartridge 130, or portions thereof, can be asymmetrical even if housing 110 is substantially symmetrical. In the illustrated example, a cartridge 130 is seated within a portion of the housing and may be aligned substantially along the first axis. As described herein, cartridge 130 may contain a heating element to heat liquid stored within the cartridge and generate the desired aerosol. Cartridge port 109 is configured to accept cartridge 130 is provided at a first end of housing 110 along the first axis, with charging cap 170 located at the opposite end of housing 110 along the first axis.

Cartridge 130 includes a shell 138 defining fluid compartment 146. Shell 138 may be coupled with mouthpiece 132 having at least one vapor tube 136 configured to allow vapor to exit cartridge 130. Shell 138 can be configured to rest against or above a portion of housing 110 when cartridge 130 nests with cartridge port 109 and may or may not include geometry complementing the contours of housing 110. To allow airflow between mouthpiece 132 and one or more of shell 138 and/or membrane 142 (described below), mouthpiece 132 can include one or more spacers 134 which mechanically interfere with a closed fit. In examples, a vapor- or fluid-permeable material (e.g., felt, wadding and the like) can be placed in the gap created by spacers 134, which can distribute vapor, stop droplets or burnt residue, filter vapor, and/or cool vapor. In examples, a mouthpiece cover or guard can be provided to plug the at least one vapor tube 136 and cover some or all of mouthpiece 132 to provide for sanitary protection of the mouthpiece when not in use. While vapor tubes 136 are shown as cylindrical, other cross-sectional shapes can be used. In embodiments where two or more vapor tubes 136 are present, multiple cross-sectional shapes can be used in symmetrical or asymmetrical arrangements. While two vapor tubes 136 are shown in a symmetrical arrangement, asymmetrical arrangements can be utilized (e.g., disposing one or more vapor tubes 136 to one side but not another along the second axis 2). Mouthpiece 132 can have a curved contour in at least the plane defined by the first axis 1 and second axis 2. Edges of mouthpiece 132 can be curved, and mouthpiece 132 (and/or a shell 138 and/or fluid compartment 146 to which mouthpiece 132 is connected) can have a profile suitable to allow inhalation therefrom either by placing a mouth against mouthpiece 132 or by placing mouthpiece 132 partially or entirely in a user's mouth. Mouthpiece 132 can include one or more recesses, which can surround one or more of vapor tubes 136. Such recesses can allow vapor to distribute from vapor tubes 136 before inhalation or serve other functions.

In embodiments, mouthpiece 132 can be fluidly coupled to a sensor for detecting suction or a deviation from a pressure baseline. The sensor can be coupled to circuit board 116 and initiate heating and vaporization of fluid in cartridge 130 based on the detection of suction or changes in pressure. In this manner, vaporization can be controlled to times when the user is actively seeking to utilize vaporizing device 100. In embodiment, a microphone can be used alone or in conjunction with a pressure sensor to detect suction or changes in pressure to actuate heating. In embodiments, blowing or ceasing suction can stop heating or serve as an "off" function for the device. In alternative or complementary embodiments, the microphone can utilize sound, alone or in combination with suction, to enable or disable heating (or other functions of vaporizing device 100). In embodiments, a microphone or other air pressure sensor can convert air pressure to high and low levels to control electrical output. In particular embodiments, air pressure measurements from a sensor can be converted to high or low levels recognizable by a control unit that are then used to active or deactivate a heating element such as heating element 154.

As discussed, cartridge 130 defines a fluid compartment 146 that is filled with a vaporizable fluid used to simulate the act of smoking. A membrane 142 may be provided between cartridge 130 and mouthpiece 132 to provide a fluid barrier between mouthpiece 132 and fluid compartment 146. Membrane 142 can include plug 144 that extends downward from membrane 142 to be received within an opening in fluid compartment. Plug 142 may have a annular detent at the tip that compresses upon insertion and expands beyond the mouth of opening when plug is inserted into fluid chamber 146 to secure membrane to cartridge 130.

The opening in cartridge 146 may be used as a fluid port to fill fluid chamber 146. Plug 144 may be configured to secure a fluid port of fluid compartment 146, which can be plugged either following an initial filling or after refilling the compartment. According to an example, cartridge 130 is designed to be asymmetrical, i.e. lacking symmetry about an axis to ensure proper orientation during manufacture, filling and use. The asymmetry may be invoked in a variety of physical characteristics as described in more detail herein. For example, to facilitate manufacture and proper orientation for filling, the fluid port in fluid chamber 146 may be provided in an offset position where it is spaced from the center axis of cartridge 146. As best shown in FIG. 11, fluid port is offset from center axis and provided only on a single side of cartridge 130 creating a physical asymmetry in the cartridge relative to the center axis. As noted, this asymmetry facilitates orientation during manufacture by providing a visual cue, i.e. offset fluid port, that is visible to laborers or vision systems in the assembly chain to orient the cartridge for filling and final assembly. Correspondingly, membrane 142 has an offset plug 144' on one side to be inserted in fluid opening creating a similar asymmetry to facilitate its proper orientation and assembly. In the example, vapor conduit 150 is located along center axis of cartridge 130 within fluid chamber. The asymmetry created by providing a single fluid port is offset from center may prevent interference or contamination of vapor conduit 150 and/or other elements of cartridge 130.

Mouthpiece 132 may attach to fluid chamber 146 in a variety of known manners including but not limited to a mechanical fastener, such as a latch, detent, screw, interference fit and the like; a chemical fastener, such as an adhesive, a weld or other bond; or integrally forming the mouthpiece with fluid compartment as a unitary structure. In the example, a mechanical fastener is used. Fluid compartment 146 can include tabs 148 to nest with tab apertures 140 of shell 138, thereby removably coupling these elements. In alternative examples, other means of fixedly or removably joining fluid compartment 146 and shell 138 can be utilized, including adhesives, integral formation, melting, friction fits, et cetera. Fluid compartment 146 is shown with a substantially and irregularly hexagonal cross section in planes defined by second axis 2 and third axis 3, and a substantially rectangular cross section in planes defined by or first axis 1 and third axis 3. However, any other shape imagined by a designer can be used. As described, cartridge port 109 is provided with a corresponding shape to allow fluid compartment to at least partially nest with cartridge port 109 of housing 110. Fluid compartment 146 can nest at least in part in a hollow portion of cartridge port 109 of housing 110, and either be entirely contained therein when seated or protrude therefrom. As described more completely below, power from a power source such as a battery, may be delivered to heating element 154 within fluid compartment 146 by providing corresponding electrical contacts within the base of fluid compartment 146 and cartridge port 109 to energize heating element 154.

Rather than vaporizing all material in cartridge 130, limiting its length of use, or vaporizing portions of the material among all the reservoir's fluid, which can be inefficient, battery-draining, and contaminate unused fluid with residue, a vapor chamber 152 can be included in fluid compartment 146. Vapor chamber 152 allows small amounts of fluid in from the larger fluid compartment 146, isolating the fluid therein during vaporization. Vapor chamber 152 can include sloped geometries, which can be sloped or curved, to retain more fluid closer to heating element 154 and/or prevent the buildup of vapor outside vapor conduit 150. Vapor chamber 152 can also include a mating portion for coupling vapor chamber 152 with heating chamber 156. The mating portion can include a smaller cross-section, in one or more dimensions, than other portions of heating chamber 156. Heating element 154 is contained at least in part in vapor chamber 152, or can be contained in a heating chamber 156 which is operatively coupled and in fluid communication with vapor chamber 152. Heating chamber 156 can include a complementary portion with which a mating portion of vapor chamber 152 mates or nests. Heating chamber 156 can include dimensions substantially equal to or larger than heating element 154. While heating element 154 is shown as a coil wrapped around a cylinder or post and arranged lengthwise substantially along the second axis 2 with one or more electrically conductive portions directed toward pogo pins 166 along first axis 1, other heating element configurations can be employed without departing from the scope or spirit of the innovation. Vapor conduit 150 extends from vapor chamber 152 through fluid compartment 146, membrane 142, and shell 138 to establish fluid communication with mouthpiece 132, isolating the vapor from cooler fluid and preventing its dispersion or escape prior to inhalation. While shown to be cylindrical and centered, vapor conduit 150 can take any shape or cross-section imagined by a designer and may be offset or arranged asymmetrically as can be imagined by a designer. Vapor conduit can be fixedly disposed between two receptacles of cartridge 130 and prevent from moving by such receptacles or the geometry of cartridge 130.

Fluid compartment 146 is closed opposite the mouthpiece-end (along the first axis) by connector 158. Connector 158 provides an anchor for vapor chamber 152 and associated elements and provides electrical communication through fluid compartment 146 via one or more pogo pins 166. Pogo pins 166 provide a conductive path from battery 118 and associated circuitry to heating element 154. While pogo pins 166 are shown as two posts substantially centered, asymmetrical arrangements with even or odd numbers of pogo pins 166 can be utilized without departing from the scope or spirit of the disclosure. Post collars 164 provide a fluid-impermeable path by which pogo pins 166 can pass through connector 158 to maintain electrical communication with heating element 154. Connector 158 can include protruding portions (e.g., directed toward a mouthpiece end along first axis 1) for connecting connector 158 to one or more of heating chamber 156, vapor chamber 152, and/or other elements within housing 110. Connector 158 can include a base having a larger cross-section (in planes defined by second axis 2 and third axis 3) than other portions, which can nest in, cover, or wrap around an end of fluid compartment 146. In embodiments, connector 158 need not be symmetrical, and can include protruding portions or other subcomponents in uneven or non-centered configurations. Connector 158 also includes cartridge magnet recesses 159 to receive cartridge magnets 160 and 161. First cartridge magnet 160 is configured to attract first housing magnet 120 and repel second housing magnet 121 when coupling cartridge 130 with the vaporizing device. Second cartridge magnet 161 is configured to attract second housing magnet 121 and repel the first housing magnet 120 when coupling cartridge 130 and the vaporizing device. Put another way, cartridge magnets are substantially oriented in a polar configuration such that cartridge 130 will attract to, seat in, and resist decoupling when inserted in a first manner, and cartridge 130 will repel and avoid coupling when inserted in a second matter substantially 180 degrees from the alternative configuration (as measured in the plane defined by the second and third axis).

Fluid compartment 146 defines a shape of a portion of cartridge 130. As illustrated, fluid compartment 146 can have a substantially and irregularly hexagonal cross section (i.e., when viewed on a plane defined by second axis 2 and third axis 3). Other cross-sections can utilized as might be imagined by a designer, so long as they are dimensionally less than or substantially equal to the interior dimensions of a hollow portion of housing 110. In alternative embodiments, fluid compartment 146 (or other portions nesting in or mating with housing 110) may have a different profile, shape, form factor, et cetera, than housing 110 but still matches a hollow portion defining cartridge port 109 (e.g., a fluid compartment of a cartridge can be an irregular hexagon matching an irregular hexagon cartridge port while the housing has a pyramid shape). Shell 138 can take any shape, but as illustrated includes a protruding portion configured to match cutout portion 111. Shell 148 (or other elements herein) can be formed of insulating materials to prevent the external surfaces of the vaporizing device from becoming hot. In alternative embodiments, shell 138 includes no protruding portion. Shell 138 can change in cross-section throughout its dimensions, flaring or tapering, and changing from angled edges to rounded edges (e.g., areas near mouthpiece 132 can be rounded for In still further embodiments, no shell 138 need be included, and mouthpiece 132 can be connected directly to fluid compartment 146.

As illustrated, cartridge 130 need not be symmetrical. Various elements therein need not be centered or equally distributed, and cartridge 130 need not have a symmetrical form factor about any axis. Moreover, first cartridge magnet 160 and second cartridge magnet 161 cause asymmetry in cartridge 130 given their substantially opposing polarities.

Continuing to the vaporizing device, housing 110 provides energy storage and control for operating heating element 154 thereby providing vaporizing effects. Housing cap 112 can isolate the interior of housing 110 from cartridge 130. In examples, housing cap 112 can include a gasket or other seal to fluid-proof housing 110, protecting its electrical components from damage as a result of fluid leaked from the cartridge 130 or other sources. Housing cap can be a solid cap with a substantially planar top surface (or other shape for interfacing mechanically and electrically with cartridge 130) and a bottom surface for retaining and arranging components within solid or filled portions of housing 110. In examples, housing cap 112 can include flexible tack 113. Flexible tack 113 can be asymmetrically arranged to one side of housing 110. In embodiments, flexible tack 113 can be used to retain a seal overlaying or integrated with housing cap 112. Such a seal can plug into or wrap around flexible tack 113, then extend up a side and around housing cap 112 with pogo bases 115 and magnets 119 extending therethrough. In embodiments, flexible tack 113 can be constructed of an air tack silicon or similar material.

Electrical base 114 is also included in housing 110. Electrical base 114 is operatively coupled with one or more pogo bases 115 which pass through housing cap 112 to contact pogo pins 166, thereby providing power from battery 118 to heating element 154. Electrical base 114 as illustrated can include a substantially planar bottom portion on which pogo bases 115 rest. In embodiments where pogo pins 166 are asymmetrical, pogo bases 115 can be similarly arranged. Battery 118 can be sized to fit within housing 110, and may be sized to maximize its battery capacity therein (e.g., occupying all space available, or matching alternative geometries to optimize capacity or efficiency). In embodiments, battery 118 can be designed to use less than the volume defined by housing 110 in one or more dimensions to be arranged alongside other elements in the same space in two or more dimensions (e.g., circuit board 116 and battery 118 can partially or wholly overlap along one or more axes). Further, battery 118 (or other elements herein) can be arranged to fit inside frame 122. In embodiments, two or more batteries or battery cells can be represented by battery 118. Battery 118 may be a battery permanently affixed in housing 110, or may be a removable or replaceable battery.

Housing 110 also contains circuit board 116. Circuit board 116 receives input from users and controls, by user input and automatically based on feedback from at least heating element 154, power supplied to heating element 154. In this manner, vapor is produced in a controlled manner, can be toggled on and off, and in examples can be provided at higher or lower temperature. Circuit board 116 can be shaped according to the dimensions of housing 110, Frame 122 can support or position various elements within housing 110. Charging contacts can provide electrical communication to pogo contacts 178 within charging interface 176, allowing charging of battery 118. In embodiments, other numbers of pogo contacts 178 can be utilized, and may be arranged asymmetrically.

Housing 110 can also contain charging board 123 (for charging, e.g., a light for indicating a device status), cover 124, and magnet 126 (e.g., for securely nesting vaporizing system 100 in a charger such as charger 190). Elements within housing 110 can be designed to nest in a reduced volume defined by frame 122. Frame 122 can take various shapes that can utilize the outer portions of a volume defined by housing 110, or can be sized to dimensions less than the inner dimensions of housing 110 to arrange elements which do not stack neatly therein or provide air gaps between elements therein or elements and/or housing 110. Frame 122 can include asymmetrical aspects or asymmetrically arrange elements within housing 110. In embodiments, one side of frame 122 is solid (e.g., has a planar shape or surface contouring the walls of housing 110 but is open on the other side exposing, e.g., circuit board 116 and battery 118. In alternative embodiments, frame 122 can be fully skeletonized, providing support only about a perimeter of elements housed within housing 110. Frame 122 can be constructed of various materials (e.g., metal, plastic, carbon fiber, et cetera) and may be constructed of a different material than that used for housing 110. In embodiments, a seal about housing cap 112 or other elements integrated in frame 122 provides a friction fit to prevent its removal from housing 110. In embodiments, frame 122 is joined with housing cap 170, and can be removed from housing 110 by pulling downward on the first axis 1. In embodiments, wires, circuitry, printed circuit board tape, or other electrically communicative elements can run along one or more surfaces of frame 122 to avoid interference with other elements contained therein.

First housing magnet 120 and second housing magnet 121 are positioned at the top of frame 122, and nested within housing 110. First housing magnet and second housing magnet are oriented such that substantially opposite polarities are arranged with respect to the first axis, thereby repelling cartridge 130 if improperly oriented and attracting cartridge 130 if properly oriented. In embodiments, first housing magnet 120 and second housing magnet 121 can be differently sized and/or shaped, and/or possess different magnetic flux.

On the end of housing 110 opposite cartridge 130 along the first axis, charging cap body 172 closes housing 110. Charging base 174 allows electrical communication between pogo contacts 178 and charger 190. In embodiments, a portion of charging cap body 172, a portion of housing 110 disposed immediately there above, or an intervening element can be translucent or transparent. A light emitting diode or other element can be disposed therein and provide visual signals relating to operation of the vaporizing device. For example, when charging, this portion may blink red; when charged, it may turn another color, in solid or blinking modes. Likewise, during use or disuse, battery level, device function, and other feedback can be provided by light emitted.

In examples, charging cap 170 can include one or more magnets 180 for orienting charging base in a charger based on complementary magnets of the charger. As with other magnets herein, the polarities of magnets 180 in charging cap 170 can be oriented in substantially opposite orientation, matching complementarily biased magnets in charger 190, thereby attracting and seating charging cap 170 in charger 190 when properly oriented and repelling and preventing seating of charging cap 170 in charger 190 when rotated out of proper orientation. Alternatively or complementarily to a magnetic or friction-fit arrangement between charging cap 170 and charger 190, charging cap 170 can include geometry (e.g., recesses of particular sizes or locations) to match complementary geometry of charger 190 (e.g., protrusions mating with the recesses) to securely seat charging cap 170 in charger 190. Charging cap 172 can take various shapes that may substantially match or deviate from the shape of housing 110 in one or more dimensions. In embodiments, charging cap 172 can have a shape different from housing 110 and be shaped to mate with charger 190. In embodiments, a plurality of charging caps 170 can be provided to mate with different chargers, each matching a shape or interface of housing 110 on one side and transitioning to a different shape to match charger 190 on another.

Charger 190 includes charging port 192 that receives charging cap 170 and includes electrical contacts to provide electrical power to vaporizing devices via charging cap 170 and its associated elements; charging extension 194 that couples the charging port to a power source; and power source 196. While power source 196 is shown as a Universal Serial Bus (USB) interface, it is understood that any source of power can be used without departing from the scope or spirit of the innovation.

Vaporizing devices herein can include additional elements without departing from the scope of the disclosure. For example, light emitting diodes (LEDs) or other visual interface elements can be used to readily depict to users an amount of fluid remaining in cartridge 130, an amount of charge remaining on battery 118, an operation state of a vaporizing device (e.g., active, inactive, hot, cold), et cetera. In examples, multiple visual interfaces can be included, such as cutouts showing portions of a seated cartridge, various LEDs or lights, screens, et cetera.

In embodiments, a multicolored LED 125 can be built into housing 110 or be positioned between elements thereabout (e.g., housing 110 and charging cap body 172, housing 110 and cover 124). In embodiments, LED 125 can be within or behind a translucent portion, fiber optic portion, or other light-transmitting material. In this manner, LED 125 can turn on or off, brighten or dim, change color, blink, et cetera, to indicate a status of one or more aspects of vaporizing system 100. Examples of information conveyed by LED 125 can include a charging or battery status (e.g., fully charged, partly charged, battery low), device power status (e.g., on, off, heating or producing vapor, cool or not producing vapor), cartridge fill status (e.g., vaporizable liquid full, partially filled, nearly empty or empty), connectivity status (e.g., paired to app, pairing, not paired), physical connection statuses (e.g., properly or improperly seated cartridge, properly or improperly seated for charging), et cetera. LED 125 can also assist with location of vaporizing device 100 or signaling by flashing, blinking, changing colors, et cetera, when a device location function is actuated.

In embodiments, circuit board 116 (or other electronic elements) can include a wireless communication component such as a wireless transmitter or wireless transceiver. The wireless component can be used to pair vaporizing device 100 with another device (e.g., via Bluetooth or near other field communication, including but not limited to RF, Zigbee, IR and the like) or network (e.g., WiFi, cellular network). Based on this connection, data concerning the status and function of vaporizing device 100 can be provided to an interface (e.g., mobile app, website, widget) available to a user. In embodiments, settings for vaporizing device 100 can also be controlled on the interface. Settings can include, e.g., operating temperature(s), preferences or enablement of device location functionality (see infra), notification enablement (device sounds and lights, notifications to app, notifications to e-mail, et cetera, based on device location, usage, battery, fluid, function or degradation, et cetera), power saving modes (e.g., when radio is enabled based on the presence or absence of cartridge 130, heating and cooling schemes), and others.

In embodiments, the interface can include a "find my device" function. The "find my device" function may cause vaporizing device 100 to emit a sound or vibration (e.g., from a speaker integrated in circuit board 116 or other portions of vaporizing device 100). The "find my device" function can alternatively or complementarily indicate a position or direction of vaporizing device 100 in relation to the location of the display providing the interface (e.g., a user's mobile phone or laptop). Other information communicated can include a battery or charging status, time to charge, battery time left, cartridge or liquid status, time to fluid empty, improper cartridge seating, improper charging seating, device function (e.g., heating, cooling, producing vapor, not producing vapor, malfunction), et cetera.

To preserve battery, pairing with a device or network can be conducted in a manner reducing or limiting the "on time" of a radio associated with vaporizing device 100 (integrated into circuit board 116, operatively coupled with circuit board 116 as a separate element). The wireless component can be awakened for short spans of time (e.g., 0.5 second) to allow searching, discovery, and linking of the wireless component with another element. Further elements of circuit board 116 can include testing elements for the battery, measuring voltage or current and converting analog to digital for acquisition by electronic components in communication with wireless component. Actuation of functionality to locate vaporizing device 100 using a user device can provide, on an interface displayed with the user device, arrows, acousto-optic instructions, sounds or haptic feedback which changes is frequency, intensity, or rate based on proximity, et cetera.

Battery can also be preserved by other manners. The insertion or removal of cartridge 130 can serve as a power enabling "on" or "off" function. In an embodiment, vaporizing device 100 remains in a dormant state (e.g., no power being drawn or electricity used) after assembly until cartridge 130 is inserted for a first time, at which time the radio associated with vaporizing device 100 is enabled for the first time (e.g., first Bluetooth ping). In an embodiment, the radio can return to a dormant state after cartridge 130 is removed from vaporizing device 100. In an alternative embodiment, the radio can remain active after removal of cartridge 130 from vaporizing device 100. In embodiments, the customer can change a setting (e.g., using an application or interface described herein) to determine whether the device is dormant or if the radio should remain active when cartridge 130 is removed after an initial use.

In embodiments, a system can include vaporizing device 100 (or other vaporizing devices disclosed herein) having a wireless communication component. The system can also include an application or user interface configured to provide one or both of information about the vaporizing device and control of the vaporizing device. The user interface can include text or graphical representations of device status or information as discussed herein, and may also allow the user to control the device or modify its functions or settings as disclosed herein.

FIGS. 12-19 show various views of cartridge 130 including the elements or associated components described herein.

Figure 20A:
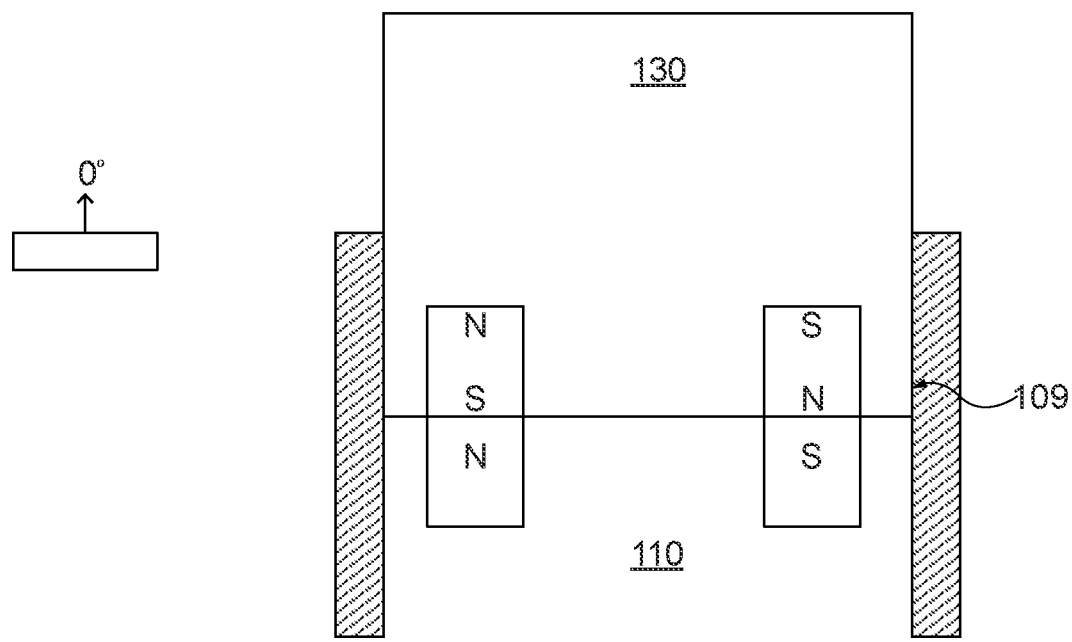
FIG. 20A illustrates magnets arranged to seat and secure a cartridge in a vaporizing device according to a particular orientation.
Figure 20B:
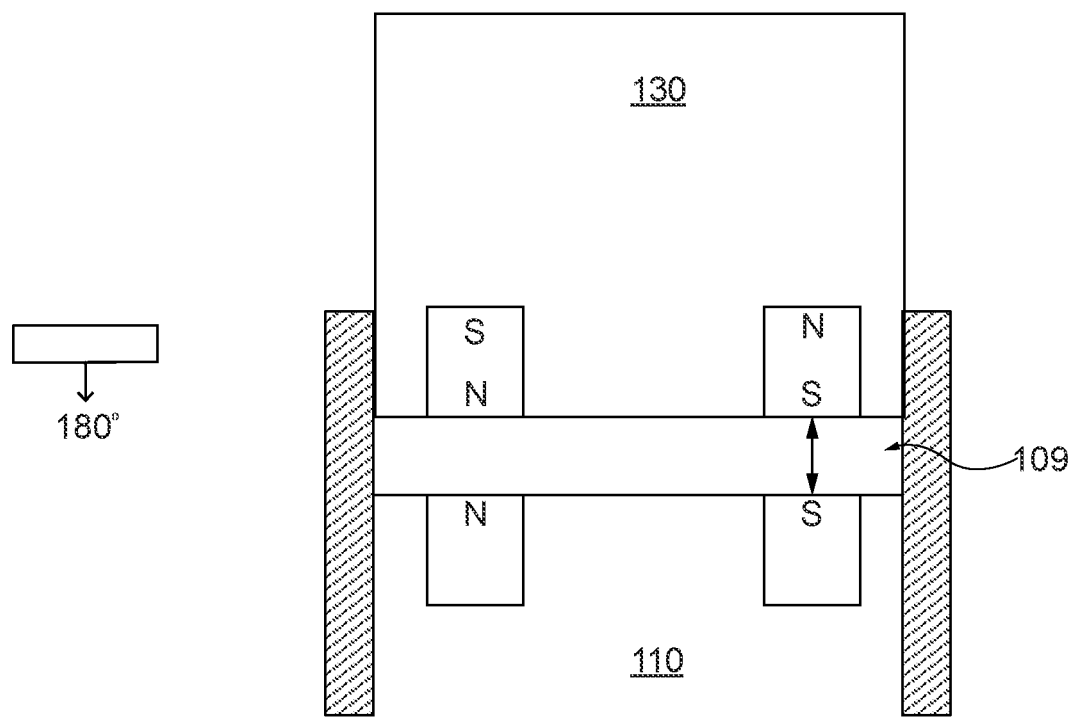
FIG. 20B illustrates magnets arranged to repel and prevent seating of a cartridge in a vaporizing device according to a particular orientation.

FIGS. 20A and 20B show a block diagram of magnet orientations described herein. Particularly, FIG. 20A shows cartridge 130 properly oriented with respect to housing 110, matching polarities of the magnets of cartridge 130 to opposite polarities of housing 110, creating attraction and seating cartridge 130 properly for use with the vaporizing device of housing 110. When cartridge 130 is rotated 180 degrees from the orientation of FIG. 20A in FIG. 20B, the same polarities are aligned between the magnets of cartridge 130 and housing 110, creating a repelling force and preventing the seating of cartridge 130 in housing 110. By enforcing this alignment, users can be assured that the cartridge is properly seated and will receive power as expected from the vaporizing device. This can be particularly important where electrical contacts of multiple polarities are included, where cartridges or vaporizing devices have asymmetrical designs, or where accurate, consistent contact between the electrically communicative components of the vaporizing device and cartridge 130 are desired or needed for use and/or longevity.

Figure 21:
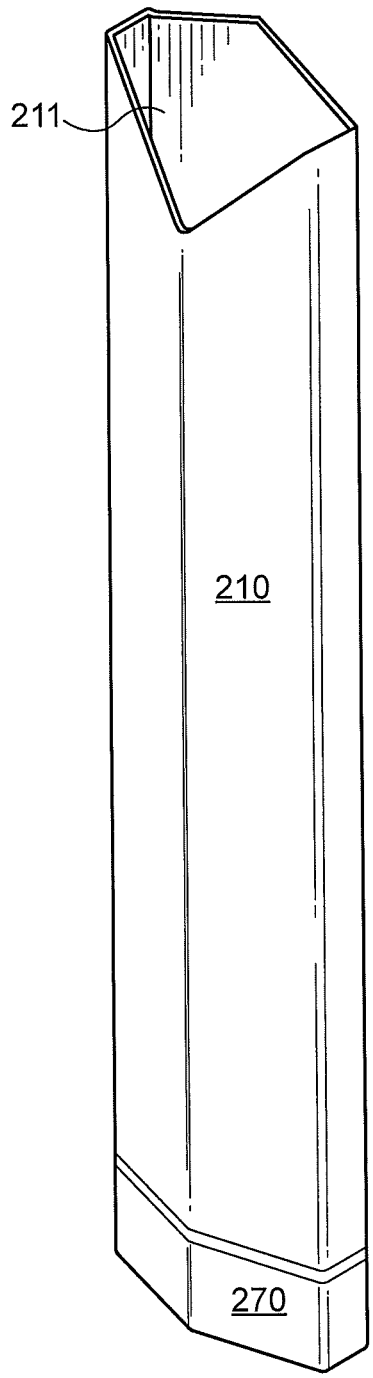
FIG. 21 illustrates a view of an example vaporizing device.
Figure 22:
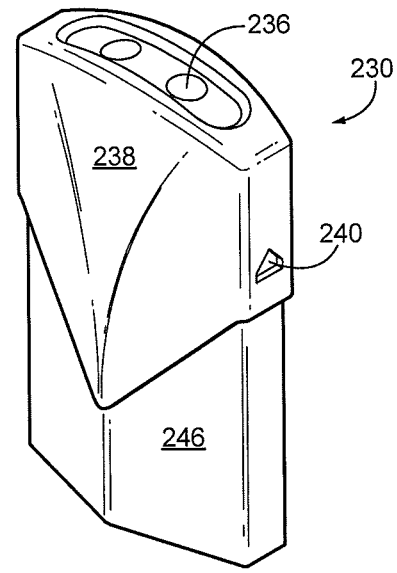
FIG. 22 illustrates a view of an example cartridge.
Figure 23:
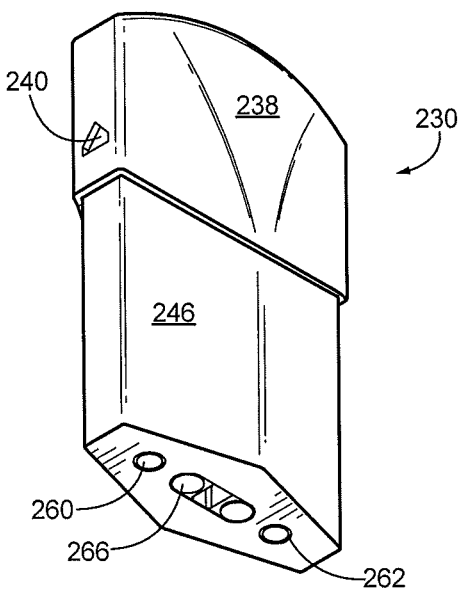
FIG. 23 illustrates another view of an example cartridge.

As shown in the figures, housing 110 can include a cutout portion 111 with which an extension of shell 138 mates when cartridge 130 is coupled with the vaporizing device. However, as can be appreciated in FIGS. 21-23, the cutout portion 211 and extension may not be symmetrical about one or more of the three axes. For example, housing 210 can include a cutout portion 211 on one side of a first end along the first axis, but not on a side opposite (e.g., by the third axis) on the other. Cartridge 230 can be similarly configured, thereby adding mechanical interference as an alternative or complementary mechanism for proper orientation of cartridge 230 in housing 210. The example(s) of a vaporizing device in FIGS. 21-23 can also include, e.g., charging cap 270, and/or other elements described elsewhere herein, re-numbered as shown in the relevant figures. The example(s) of a cartridge 230 in FIGS. 21-23 can also include, e.g., vapor tube(s) 236, shell 238, tab aperture(s) 240, fluid compartment 246, first and second cartridge magnets 260 and 262, pogo pin(s) 266, and/or other elements described elsewhere herein.

In embodiments, housing 210 can be asymmetrical beyond the differences in cutout portion 211 and magnet bias. For example, housing 210 can be flared, tapered, stepped, or having different contours or shapes when comparing a first side to its opposite side (in one or more of height, width, and depth). Cartridge 230, or portions thereof, can be shaped to join with the asymmetrical housing 210. Further, cartridge 230, or portions thereof, can be asymmetrical even if housing 210 is substantially symmetrical.

Examples herein can include a method of using the apparatuses disclosed in FIGS. 1 to 23. An example method can include providing a housing for a vaporizing device having a first housing magnet and a second housing magnet. The first housing magnet is substantially oriented in a first polar configuration, and the second housing magnet is substantially oriented in a second polar configuration. The second polar configuration is substantially opposite the first polar configuration. The method can also include providing a cartridge configured to contain fluid for vaporization. The cartridge is configured to mate with the housing, and has a first cartridge magnet and a second cartridge magnet. The first cartridge magnet is configured to attract the first housing magnet and repel the second housing magnet when coupling the cartridge with the housing, and the second cartridge magnet is configured to attract the second housing magnet and repel the first housing magnet when coupling the cartridge with the housing. The method also includes coupling the cartridge with the housing according to polarities of the magnets.

Further aspects herein can include a method for producing the apparatuses disclosed in FIGS. 1 to 23. Various components can be constructed and assembled in a frame. A charging cap and a housing cap can be attached to the frame, and the frame and charging cap assembly can be inserted into a housing. Magnets can be arranged in the charging cap and housing cap to properly seat cartridges in the vaporizing device or the vaporizing device in charger. Similarly, a cartridge can be constructed by producing the elements described herein, assembling a fluid compartment including the various subcomponents contained therein, filling the fluid compartment, sealing the fluid compartment, and assembling the shell and mouthpiece over the top of the fluid compartment. Magnets can be provided in the cartridge with appropriate polarities to properly seat the cartridge in the vaporizing device.

While aspects of the present disclosure have been particularly shown and described with reference to the examples above, it will be understood by those skilled in the art that various combinations of the disclosed aspects or additional aspects may be contemplated by the modification of the disclosed machines, systems and methods without departing from the spirit and scope of what is disclosed. Such aspects should be understood to fall within the scope of the present disclosure as determined based upon the claims and any equivalents thereof.

What is claimed is:

1. A personal vaporizer, comprising:
a housing defined by a height extending along a first axis, a width extending along a second axis, and a depth extending along a third axis, having at least a front wall, a back wall, and two side walls;
a power supply disposed within the housing;
a charging assembly configured to charge the supply disposed on a bottom end of the housing along the first axis;
a cartridge port configured to accept a cartridge disposed on a top end of the housing along the first axis, wherein the cartridge is asymmetrical is about an axis of rotation including a first cartridge magnet and a second cartridge magnet located on opposite sides of the axis and spaced from each other, wherein the first cartridge magnet has an outward facing magnetic pole and the second cartridge magnet has an outward facing magnetic pole that is opposite to the first cartridge magnet outward facing magnetic pole;
a first housing magnet of the cartridge port substantially oriented in a first polar configuration;
a second housing magnet of the cartridge port substantially oriented in a second polar configuration, wherein the second polar configuration is substantially opposite the first polar configuration;
an electrical contact of the cartridge port configured to establish electrical communication when the cartridge is seated in the cartridge port; and
a frame arranging the power supply, the charging assembly, the first housing magnet, the second housing magnet, and the electrical contact within the housing.

2. The personal vaporizer of claim 1, comprising:
the cartridge;
a fluid compartment of the cartridge;
a shell of the cartridge, wherein the cartridge dimensions are defined by the fluid compartment and the shell, wherein the fluid compartment and the shell are configured to seat in the cartridge port, wherein the fluid compartment seats in the housing by nesting at least in part in a substantially hollow portion of the cartridge port;
a first cartridge magnet of the cartridge configured to attract the first housing magnet and repel the second housing magnet when coupling the cartridge with the housing; and
a second cartridge magnet of the cartridge configured to attract the second housing magnet and repel the first housing magnet when coupling the cartridge with the housing.

3. The personal vaporizer of claim 2, comprising:
a cutout of the housing; and
an extension of the cartridge configured to mate with the cutout when the cartridge is coupled with the housing.

4. The personal vaporizer of claim 3, wherein the cutout and the extension are not symmetrical about one or both of the first axis and the second axis.

5. The personal vaporizer of claim 1, wherein the power supply is a rechargeable battery.

6. The personal vaporizer of claim 5, comprising:
a fluid port formed within the cartridge, wherein the fluid port is offset from the axis of rotation;
a membrane provided between the fluid compartment and the mouthpiece, a portion of the membrane covering the fluid port and including a downward extending plug received in the fluid port.

7. The personal vaporizer of claim 5, comprising:
a charging cap in electrical communication with the battery.

8. The personal vaporizer of claim 7, comprising:
a charging contact of the charging cap configured to establish electrical communication with a charger.

9. The personal vaporizer of claim 8, comprising:
a charging geometry configured to mechanically arrange the charging cap in the charger.

10. The personal vaporizer of claim 8, comprising:
the charger, wherein the charger is configured to capture at least a portion of the charging cap, and wherein the charging contact is configured to communicate electrically with the charger when at least the portion of the charging cap is seated in the charger.

11. The personal vaporizer of claim 1, wherein the cartridge includes a shell having a first side and a second side relative to an axis of rotation, wherein the first side includes a downward protrusion and the second side includes a flat edge, wherein the housing includes a first recess that receives the protrusion on a first side thereof, and the housing includes a flat edge on a second side that abuts the flat edge on the cartridge when the protrusion is received in the first recess.

12. The personal vaporizer of claim 11, comprising:
at least one offset extending from the mouthpiece configured to provide an air gap between the mouthpiece and the fluid compartment.

13. The personal vaporizer of claim 11, comprising:
an electrical heating element of the cartridge.

14. The personal vaporizer of claim 13, comprising:
a pogo pin extending through a body of the cartridge configured to provide electrical communication between the electrical contact and the electrical heating element.

15. The personal vaporizer of claim 13, wherein the electrical heating element is arranged along the second axis.

16. The personal vaporizer of claim 13, comprising:
a vapor chamber of the cartridge, wherein the electrical heating element is disposed within the vapor chamber.

17. The personal vaporizer of claim 16, comprising:
a vapor conduit establishing fluid communication between the vapor chamber and the mouthpiece.

18. The personal vaporizer of claim 17, comprising:
a fluid-permeable material arranged between the vapor conduit and the mouthpiece.

\* \* \* \* \*